United States Patent [19]

Belly et al.

[11] Patent Number: 5,843,793

[45] Date of Patent: Dec. 1, 1998

[54] CONTAINER FOR STAINING OF CELLS AND TISSUES IN COMBINATION WITH A ROLLER AND A SUPPORT

[75] Inventors: Robert Troconis Belly; John Robert Chemelli, both of Webster; Michele McWilliams Steinmann, Rochester, all of N.Y.

[73] Assignee: Johnson & Johnson Clinical Diagnostics, Inc., Rochester, N.Y.

[21] Appl. No.: 728,586

[22] Filed: Oct. 10, 1996

Related U.S. Application Data

[60] Provisional application No. 60/005,467 Oct. 16, 1995.

[51] Int. Cl.$^6$ .......................... G01N 33/558; G01N 22/00
[52] U.S. Cl. .......................... 436/514; 422/58; 422/68.1; 435/287.1; 435/287.2; 435/810
[58] Field of Search .............................. 436/514; 422/58, 422/68.1, 82.05, 82.09, 222, 220, 206; 435/287.1, 810, 287.2

[56] References Cited

U.S. PATENT DOCUMENTS

| | | | |
|---|---|---|---|
| 3,654,091 | 4/1972 | Binnings et al. | 195/139 |
| 3,770,382 | 11/1973 | Carter et al. | 23/253 R |
| 3,785,771 | 1/1974 | Luchsinger et al. | 23/230 R |
| 4,659,677 | 4/1987 | Glover et al. | 436/174 |
| 5,229,297 | 7/1993 | Schnipelsky et al. | 436/94 |
| 5,258,314 | 11/1993 | Skerratt | 436/165 |
| 5,288,463 | 2/1994 | Chemelli | 422/58 |
| 5,290,518 | 3/1994 | Johnson | 422/58 |
| 5,593,065 | 1/1997 | Harrold | 222/94 |

OTHER PUBLICATIONS

Findlay et al. 1993, Cln. Chem. (Wash. D.C.) 39(9): 1927–33.

*Primary Examiner*—James C. Housel
*Assistant Examiner*—Jennifer Shaver
*Attorney, Agent, or Firm*—Dana M. Schmidt

[57] ABSTRACT

A flexible container containing pre-deposited reagents, comprising a plurality of temporarily sealed, breakable compartments dispersed in the container, each compartment containing a reagent useful for immuno-assaying, and each compartment comprising opposed confining walls at least one of which is sufficiently flexible as to allow the compartment to be compressed in the presence of an adequate external force, external outlets in the container for the contents of said compartments, passageways extending from each of the compartments to the outlets, each of the outlets terminating in a platform that supports a drop of at least 10 $\mu$L as a pendant drop, the platforms of at least two of the outlets being adjacent so as to form between them an exterior angle with respect to each other sufficient to cause drops pendant therefrom to substantially uniformly intermix.

10 Claims, 3 Drawing Sheets

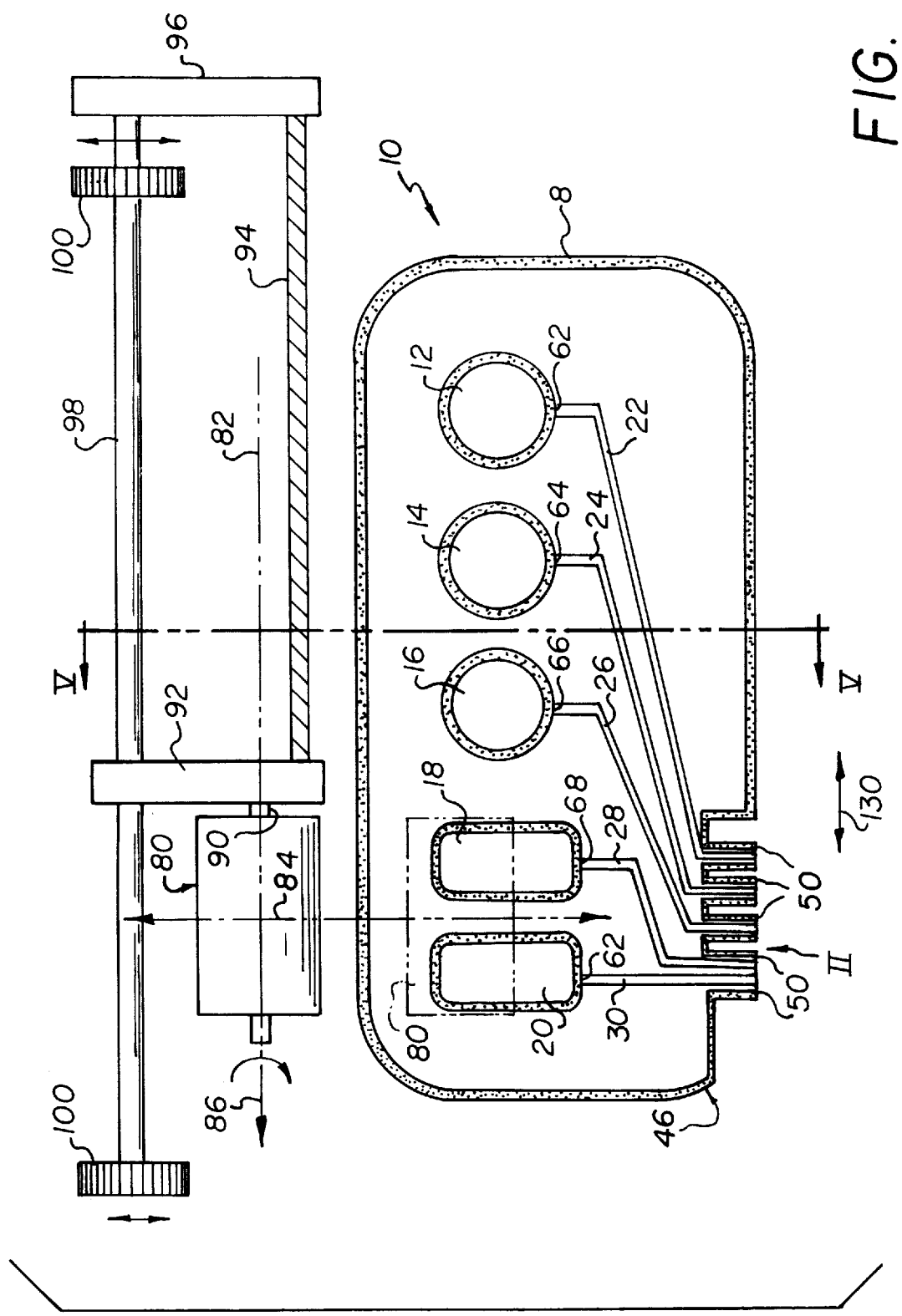

5,843,793

CONTAINER FOR STAINING OF CELLS AND TISSUES IN COMBINATION WITH A ROLLER AND A SUPPORT

CROSS-REFERENCE TO RELATED APPLICATION

This application is a non-provisional application of, and claims the benefit of, U.S. Provisional Application Ser. No. 60/005,467, filed on Oct. 16, 1995, entitled: Container for Staining of Cells and Tissues in Combination With a Roller and a Support.

FIELD OF THE INVENTION

This invention relates to the field of flexible containers of reagents used to provide staining reactions, and specifically, to provide only the amounts actually needed without storing exposed, unused reagents for long periods.

BACKGROUND OF THE INVENTION

In wet assay analyzers, it has been customary to provide liquid reagents in bottles, and then to aspirate out reagents into pipettes which dispense them into cuvettes containing patient sample, or onto some other kind of sample support. One problem among others is that the reagent bottles are supplied with an overabundance, and once opened, tend to have only a finite useful lifetime. As a result, excess, unused reagent has to be thrown out when an opened bottle ages past its posted lifetime. This is particularly a problem for expensive reagents, such as antibodies.

Yet another problem with such analyzers has been their unsuitability for handling cell-staining operations, given the fact that cell-staining is usually done on glass slides. Although U.S. Pat. No. 3,654,091 to Binnings discloses an analyzer for processing glass slides, it does so using the unsatisfactory bottled reagent concept described in the previous paragraph.

It is true that containers are known in the art that have reagents pre-deposited within them in initially separated compartments, for example, as described in U.S. Pat. No. 5,290,518. Although those reagents can be intermixed at the time of the test (for reagent stability) within the container at a chamber downstream from their temporarily sealed compartments, such intermixing works because of a) the large volumes involved and b) the exterior manipulation that is possible of the mixing chamber. If, as is often the case, neither of these two conditions exist, any small volumes fed to an interior mixing chamber do not uniformly mix, but are retained (in a single flow) as separately identifiable streams. Hence, the containers of the prior art have not been useful in all instances for intermixing two reagents therein.

SUMMARY OF THE INVENTION

We have devised a reagent container and method of use that solve the above-mentioned problems.

More specifically, there is provided, in accord with one aspect of the invention, a flexible container containing pre-deposited reagents, comprising
a plurality of temporarily sealed, breakable compartments dispersed in the container, each compartment containing a reagent useful for immuno-assaying, and each compartment comprising opposed confining walls at least one of which is sufficiently flexible as to allow the compartment to be compressed in the presence of an adequate external force,
external outlets in the container for the contents of the compartments,
passageways extending from each of the compartments to the outlets, each of the outlets terminating in a platform that supports a drop of at least 10 μL as a pendant drop,
the platforms of at least two of the outlets being adjacent so as to form between them an exterior angle with respect to each other sufficient to cause drops pendant therefrom to substantially uniformly intermix.

In accord with another aspect of the invention, there is provided a method of depositing reagents onto a cellular sample to immunostain said sample, comprising the steps of
a) providing said reagents in burstable compartments each of which empties via a passageway to an outlet,
b) selectively bursting said compartments in a predetermined sequence to force the contents to be ejected via the passageways and out said outlets, and
c) causing the contents of two adjacent compartments to substantially uniformly intermix at their outlets, prior to deposition onto said cellular sample.

Accordingly, it is an advantageous feature of the invention that a container and method are provided that allow for the automated staining of cells on a glass slide, with a minimum of wasted reagent.

It is a related advantageous feature of the invention that a container and a method of delivery of reagents are provided for any kind of processing, which avoid wastage that occurs when supplied in bottled form, and still provide for adequate mixing of certain reagents before they are touched off from the container.

Other advantageous features will become apparent upon reference to the following "Detailed Description", when read in light of the attached drawings.

BRIEF DESCRIPTION OF THE DRAWINGS

FIG. 1 is an elevational view of a container and associated apparatus constructed in accordance with the invention;

DETAILED DESCRIPTION OF THE INVENTION

Figure 3:
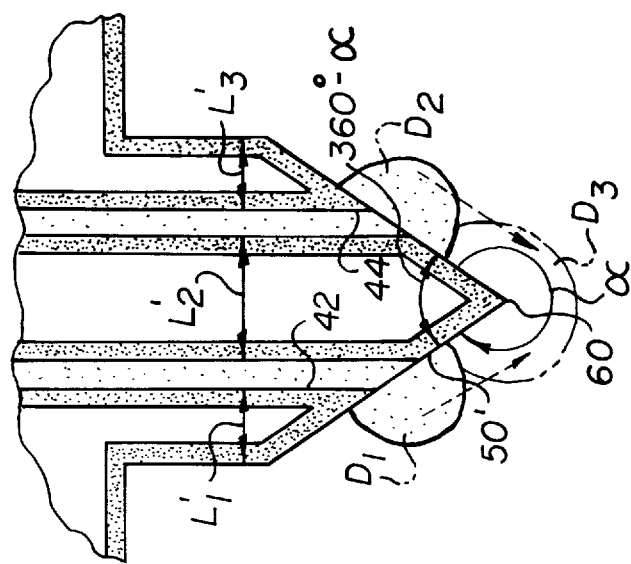
FIG. 3 is a view similar to that of FIG. 2, but illustrating an alternate embodiment of the invention.

The discussion hereinafter is of the preferred embodiments, wherein staining of cells is done on a support comprising glass slides and wherein the container has a certain preferred construction with compartments containing preferred reagents. Additionally the invention is useful for any diagnostic application, including those using reagents of any kind (in the container), applied to a support of any kind, and wherein the container has other constructions with additional compartments holding other reagents or rinses.

Immuno-staining of cells can conventionally proceed by the following steps:

1) a source of cells, such as a tissue culture, is deposited onto a support, such as a glass slide, and fixed.
2) A protein block solution is applied, and the cells plus block are incubated.
3) Excess block solution is removed.
4) An antibody to the antigen being detected, is applied to the cells on the slide, and incubated.

5) The cells are rinsed once or twice.

6) Link solution is then applied, and incubated. Avidin with four binding sites is useful as such a link, if both the antibody and the label are biotinylated.

7) Rinsing occurs again as in step 5).

8) A label is then applied, for example, an enzyme, followed by incubation.

9) Rinsing is done again, is in step 5).

10) A chromogen solution is then applied to react with any label that remains fixed to the antibody that has complexed with the target antigen, and incubated.

11) Rinsing is done again, followed by blotting to remove excess water.

12) A counterstain is applied, followed by a rinse and an application of a suitable basic solution.

13) Another rinse is applied, and if a permanent slide is desired, a mounting solution and cover slip are applied.

All of the proceeding are conventional and not described further. Those skilled in the art will appreciate that useful enzyme labels include such materials as horseradish peroxidase, beta-galactosidase, glucose oxidase, and alkaline phosphatase. Useful labels other than enzymes include fluorophores.

In addition to immunostaining, other staining reactions utilizing enzymatic detection, can be done with this container. For example, in situ hybridization and other amplification systems can be used. In situ hybridization features a DNA or RNA probe directly or indirectly labeled with an enzyme, the probe hybridizing with a nucleic acid target present in the target cells. Details for such hybridization detection of cells are found in, e.g., "Methods of Enzymology", vol. 168, edited by P. Conn, 1989, pages 753–761.

It is the advantage of this invention that solutions of the critical reagents, e.g., the protein block, the antibody, the link and the label, are applied from a pre-manufactured, disposable container which delivers only the amount required, leaving no substantial excess to be stored, exposed, in the apparatus.

More specifically, in accord with one aspect of the invention, there is provided a flexible container 10, FIG. 1, comprising opposed sheets of plastic sealed together to form compartments 12, 14, 16, 18, and 20 within the border 8 of the container, and passageways 22, 24, 26, 28, and 30, respectively, leading from the compartments to the border 8.

Figure 4:
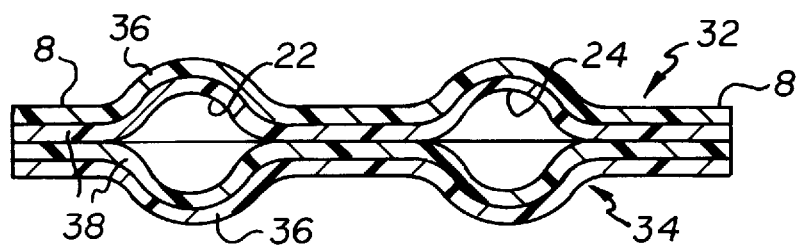
FIG. 4 is a section view taken along the line IV—IV of FIG. 3.

More specifically, FIG. 4, opposed sheets 32 and 34 are sealed together, except for the confined compartments and passageways noted above. Sealed surfaces are shown stippled, FIGS. 1–3. Preferably, each sheet 32 and 34 comprises a double-ply of plastic, namely an outer layer 36 and an inner layer 38. Any flexible material can be used, provided it will allow sheets 32 and 34 to flex inwardly when an external pressure of at least 34 kPa is applied. For example, the outer layer can comprise an oriented polyester or "Nylon" (TM) film, and the inner layer a polyethylene or polypropylene sheet. A barrier layer can be added, such as a layer of ethylene-vinyl alcohol, or a metallized polyester.

Thus, the sealed edge traverses the entire border 8 except at the outlets of the passageways. Outlets 42 & 44 are shown enlarged in FIGS. 2 and 3, and are the outlets of passageways 22 and 24, respectively, and as shown in FIG. 1, they are the first and second outlets encountered from end 46 at the left. Each outlet is surrounded by a portion of border 8 that forms a platform 50 for supporting a pendant drop of solution exiting at that outlet. The size of the drop as supported can be varied, depending on the intended solution volumes to be dispensed. At a minimum, however, the platform is shaped and sized to support and then dispense a drop having a volume of at least about 10 $\mu$L. For example, the dimensions of $L_1$, $L_2$, and $L_3$ of platform 50 can be as follows: $L_1$ and $L_3$=0.9 mm (0.035 inches) each, and $L_2$=1.5 mm, for D1 of passageway 22 and 24 of 1.5 mm each. The total platform thickness (in the dimension of the page) is about 0.2 mm (.008"). Such a platform will allow a drop to be supported pendent therefrom of a volume of 10 $\mu$L, but if the liquid dispensed from the outlet(s) of the platform is larger than about 30 $\mu$L, such liquid will fall off without having to be touched off. Thus, drops as small as 10 $\mu$L are preferably touched off from such a platform onto support 120, FIG. 5.

Figure 2:
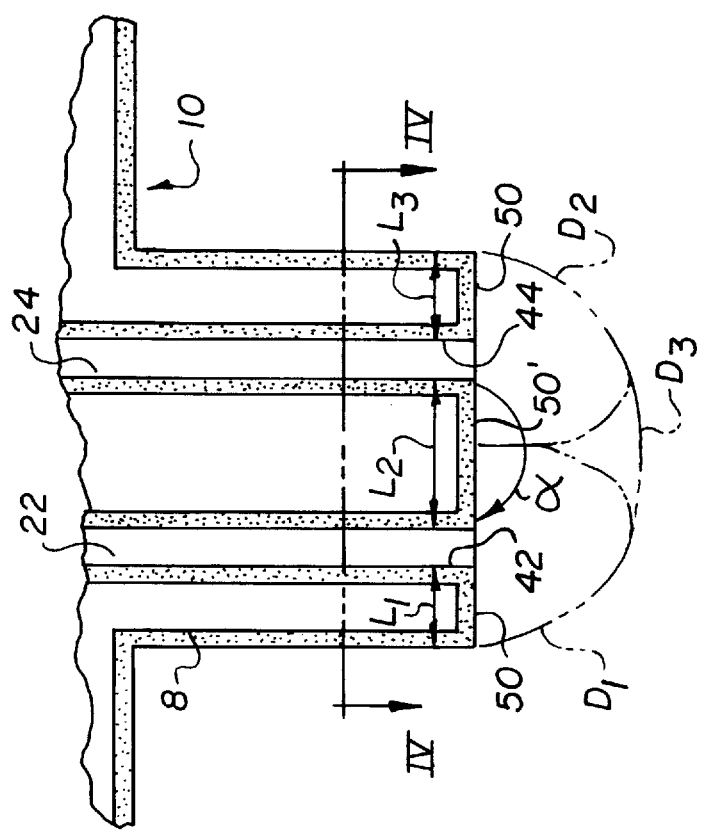
FIG. 2 is an enlarged fragmentary plan view of the portion of the container identified as II in FIG. 1.

The outlets and the platforms of passageways 22 and 24 differ from the others, FIG. 2, in that the portion 50' of the platform in between them, adjacent to the outlets of passageways 22 and 24, forms an exterior angle alpha, as shown in FIG. 2, that is sufficient to cause drops ejected from each of the two passageways to substantially uniformly intermix. This is depicted as phantom drops $D_1$ and $D_2$ as emitted, joining together to form intermixed combined drop $D_3$ (also in phantom).

Both compartments 12 and 14 empty at the same time, due to roller 80, described hereinafter, advancing over them together, as shown in phantom, FIG. 1. However, compartments 16, 18, and 20 are burst each separately from the others.

For the intended use, angle alpha is preferably between about 180°, FIG. 2, and about 330°, FIG. 3. When alpha exceeds 180°, it provides an advantage of a point 60 and a slope at each of the two outlets that causes the individual drops D1 and D2 (shown in solid, FIG. 3) to roll towards the other to intermix in the vicinity of point 60. $L_1'$, $L_2'$, and $L_3'$ in such a case can be the same as $L_1$, $L_2$, and $L_3$, so that the actual platform sizes are slightly larger for 50'.

As comparative examples, it was found that a construction of angle alpha to be less than 180° failed, as such creates a slope encouraging the drops to flow away from each other, e.g., away from portion 50', and thus they do not intermix.

Most preferably, if angle alpha is about 180 degrees, then platform 50 is oriented to be horizontal when used, rather than some non-horizontal angle, FIG. 2.

It will be appreciated, however, that each of compartments 12, 14, 16, 18, and 20 are initially temporarily sealed at their passageways, e.g. at 62 for compartment 12, FIG. 1, 64 for 14, etc., preventing the contents of the compartment from being released prematurely. The seal used to block flow into the passageway (62 for compartment 12) is not as robust as the seals around the border of the compartments and passageways. That is, seals 62, 64, 66, 68, and 70 are designed to rupture at some force such as 40 kPa (6+psi) that, however, will not rupture border seals at 8. Such a temporary seal is conventionally achieved, for the plastics of sheets 32 and 34 noted above, by creating the temporary seal at a lower sealing temperature or reduced sealer dwell time or reduced sealer pressure or some combination of all these variables to create a peelable interface seal as compared to a full strength fusion bond used elsewhere on the container. The shape of the temporary seals is preferably that shown in seals 46 and 56 of FIG. 1 of U.S. Pat. No. 5,254,479, incorporated herein specifically by reference.

The external force for rupturing these seals is applied as described hereinafter.

The contents of each of compartments 12, 14, 16, 18, and .20 depend upon the type of staining being done, and the type of solutions being used. Highly preferred, however, is the following: compartments 12 contains a primary antibody, e.g., to the antigen of interest; 14 contains the link solution, e.g., an anti-immunoglobulin solution; 16 contains label solution, e.g., a peroxidase; 18 contains a chromogen such as a substrate for the enzyme; and 20 contains hydrogen peroxide which cannot be stored with the chromogen prior to use.

Alternatively, compartment 12 contains a protein block solution, 14 contains a primary antibody, 16 contains an enzyme-labeled antibody directed to the species producing the primary antibody, preferably peroxidase labeled; and 18 and 20 remain as described above.

Still further, blister 16 can be omitted if 12 contains a protein block solution and 14 contains a primary antibody with an enzyme label.

Preferably, no sample is present since that is applied on a support described below.

Figure 5:
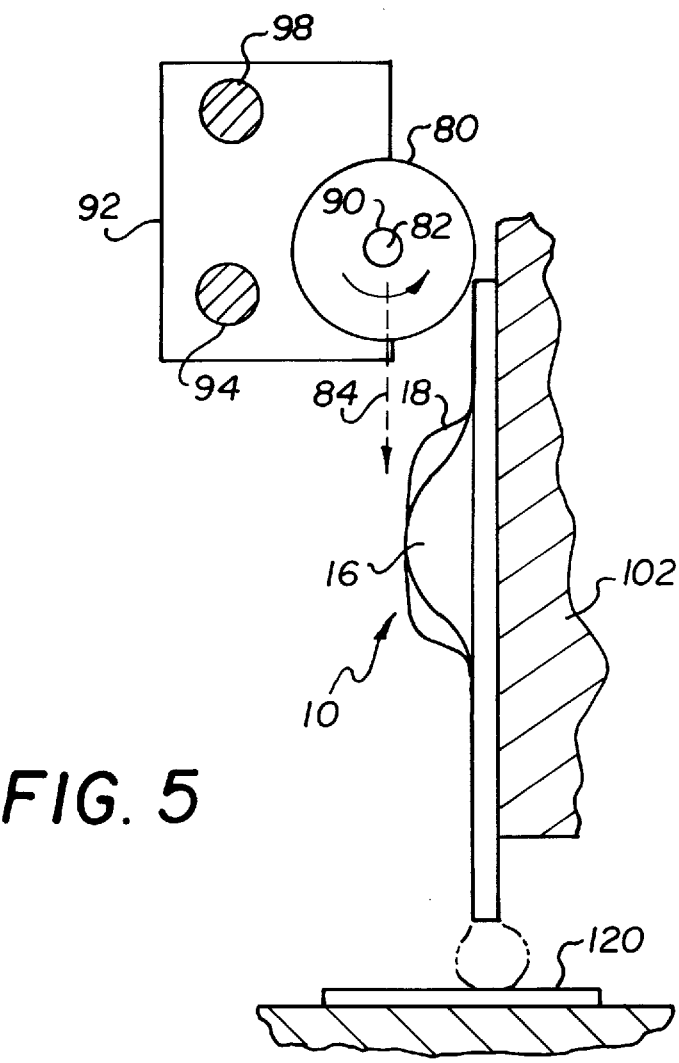
FIG. 5 is a section view taken along the line V—V of FIG. 1.

To deliver the external force necessary to rupture seals 62, 64, 66, 68, and 70, a roller 80 is used in combination with container 10, FIGS. 1 and 5. Roller 80 is mounted for rotation about an axis 82, so as to move roller 80 in the direction of arrow 84 as it rolls. Additionally, it is preferably mounted for translation, arrow 86.

These degrees of motion can be achieved by a variety of mountings. For example, axle 90 can connect roller 80 along axis 82 to a frame 92 which is screw-threaded to a lead screw 94 driven by a stepper motor, not shown. This causes translation movement, arrow 86, of frame member 92 and roller 80. Screw 94 is carried by a frame member 96 in which is journaled a second axle 98 having concentrically mounted thereon traveling pinions 100 that travel along opposed racks (not shown), to give the directional movement of axle 98 and frame 92 (in which axle 98 is journaled).

Yet another mechanism for advancing the roller is that shown in U.S. Pat. No. 5,089,233, except that only one roller is mounted on the axle, without any heating and cooling means, and the entire mechanism is rotated 90° so as to operate in a vertical, not horizontal, plane.

Container 10 is then immobilized vertically, by any suitable clamp (not shown), preferably against any rigid support 102, FIG. 5, so that roller 80 can advance, arrow 84, over the selected compartment to burst its seal and force the contained liquid to be emitted at its outlet, shown in phantom. It will thus be apparent that, also used in the combination is a support 120, such as a glass slide, onto which the contents of the compartments are dispensed (after first fixing a cell sample to support 120).

Thus, by positioning roller 80 as shown in phantom, FIG. 1, so that it compresses, when rolled, both compartments 12 and 14 simultaneously, the operator causes the contents of those two compartments to substantially uniformly intermix when they are ejected at outlets 42 and 44, respectively.

In between ejection of the contents out of each outlet, transitional movement, arrow 130, FIG. 1, is supplied between support 120 and container 10. E.g., support 120 can be moved horizontally by hand or by any suitable pusher mechanism. This insures that each passageway outlet is aligned over the spot on the support 120 bearing the cell sample, when that passageway delivers liquid to the outlet.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A flexible container containing predeposited reagents, comprising a plurality of temporarily sealed, breakable compartments dispersed in the container, each compartment containing a reagent useful for immuno-assaying, and each compartment comprising opposed confining walls at least one of which is sufficiently flexible as to allow the compartment to be compressed in the presence of an adequate external force, external outlets in the container for the contents of said compartments, said outlets being open to the atmosphere, passageways extending from each of the compartments to the outlets, each of the outlets terminating in a platform that supports a drop of at least 10 $\mu$L as a pendant drop, the platforms of at least two of the outlets being adjacent and each extending beyond their respective outlets so that the platform of one outlet contacts the platform of another of said at least two outlets so as to form between them an exterior angle with respect to each other sufficient to cause drops pendant therefrom to substantially uniformly intermix while supported by said contacting platforms.

2. A container as defined in claim 1, wherein said platforms form an exterior angle between them that is between about 180° and about 330°.

3. A container as defined in claim 1, wherein said exterior angle is greater than 180°.

4. A container as defined in claim 1, wherein said platforms of said at least two outlets occupy the first and second positions of said dispersion in said container, measured from a first exterior edge of said container.

5. A container as defined in claim 1, wherein all of said compartments and passageways are free of any sample being tested.

6. A container as defined in claim 1, wherein said at least one wall will flex in the presence of an external pressure of at least 34 kPa (5 psi).

7. A container as defined in claim 1, and further including in combination therewith, a roller and means mounting said roller to cause it to compress said compartments of said container selectively, and a support to receive the contents of said compartments as they are ejected out of the container at said outlets.

8. A container as defined in claim 1, wherein one of said compartments contains a protein block solution and another of said compartments contains a solution of an antibody specific to a surface antigen of biological cells.

9. A container as defined in claim 1, wherein one of said compartments contains a solution of an antibody specific to an antigen of biological cells and another of said compartments contains a link solution.

10. A container as defined in claim 1, wherein said contacting platforms are integrally attached to each other.

* * * * *